United States Patent
Spahn (10) Patent No.: US 8,355,928 B2
(45) Date of Patent: Jan. 15, 2013

(54) MEDICAL USER INTERFACE AND WORKFLOW MANAGEMENT SYSTEM

(75) Inventor: Martin Spahn, Erlangen (DE)

(73) Assignee: Siemens Medical Solutions USA, Inc., Malvern, PA (US)

( * ) Notice: Subject to any disclaimer, the term of this patent is extended or adjusted under 35 U.S.C. 154(b) by 394 days.

(21) Appl. No.: 12/259,345

(22) Filed: Oct. 28, 2008

(65) Prior Publication Data

US 2009/0150184 A1 Jun. 11, 2009

Related U.S. Application Data

(60) Provisional application No. 60/992,518, filed on Dec. 5, 2007.

(51) Int. Cl.
*G06Q 10/00* (2012.01)
*G06K 9/00* (2006.01)

(52) U.S. Cl. ............................. 705/3; 382/128
(58) Field of Classification Search ........................ 705/3
See application file for complete search history.

(56) References Cited

U.S. PATENT DOCUMENTS

| | | | |
|---|---|---|---|
| 5,692,125 A | 11/1997 | Schloss et al. | |
| 6,714,913 B2 | 3/2004 | Brandt et al. | |
| 7,212,986 B1 | 5/2007 | Richardson et al. | |
| 7,275,220 B2 | 9/2007 | Brummel et al. | |
| 7,310,607 B2 | 12/2007 | Brandt et al. | |
| 7,587,074 B2 * | 9/2009 | Zarkh et al. | 382/128 |
| 7,693,315 B2 * | 4/2010 | Krishnan et al. | 382/128 |
| 2005/0156125 A1 * | 7/2005 | Rimsa et al. | 250/584 |
| 2006/0167738 A1 | 7/2006 | Spear et al. | |
| 2006/0274885 A1 | 12/2006 | Wang et al. | |
| 2006/0282302 A1 | 12/2006 | Hussain | |
| 2007/0064984 A1 * | 3/2007 | Vassa et al. | 382/128 |
| 2007/0167833 A1 * | 7/2007 | Redel et al. | 600/476 |
| 2007/0197909 A1 * | 8/2007 | Kariathungal et al. | 600/437 |
| 2008/0164998 A1 | 7/2008 | Scherpbier et al. | |

* cited by examiner

*Primary Examiner* — Hiep V Nguyen
(74) *Attorney, Agent, or Firm* — Alexander J Burke (57) ABSTRACT

A medical user interface and workflow management system for use in X-ray imaging related procedures includes at least one repository. The at least one repository stores data indicating X-ray imaging related characteristics of a current medical procedure being performed including data identifying a type of procedure, comprising at least one of, (a) a current medical procedure is a cardiac related procedure and (b) a current medical procedure is an Angiography procedure. A workflow processor manages and tracks tasks being performed in a current medical procedure and adaptively selects a next task for performance following completion of a current task by selecting the next task based on the current task and in response to the X-ray imaging related characteristics. A user interface generates data representing at least one display image for presentation to a user. The at least one display image includes image elements associated with the selected next task enabling performance of the selected next task.

23 Claims, 4 Drawing Sheets

MEDICAL USER INTERFACE AND WORKFLOW MANAGEMENT SYSTEM

This is a non-provisional application of provisional application Ser. No. 60/992,518 filed Dec. 5, 2007, by M. Spahn.

FIELD OF THE INVENTION

This invention concerns a medical user interface and workflow management system for use in imaging (e.g., X-ray, MR, CT scan, Ultrasound) related procedures involving managing and tracking tasks being performed in a current medical procedure and adaptively selecting a next task for performance based on a current task and in response to imaging related characteristics.

BACKGROUND OF THE INVENTION

Known user interfaces for medical workstation or touch panels for medical diagnostic or interventional systems involving a C-arm for X-ray angiography use relatively simple and pre-defined image layouts in workflow task management. Known user interfaces typically require a user to navigate through menus and move from one displayed image to another and open option lists and boxes to support individual tasks. Known user interface systems typically allow user access to data associated with performing a large number of work tasks that are not limited to sequential tasks in a particular workflow, for example. Known user interfaces and touch panel controls for medical diagnostic and interventional systems also employ simple pull-down menus and pre-defined image layouts supporting performing work tasks. Therefore, known user interfaces are typically complicated, confusing and non-user friendly and also require more user interactions such as mouse clicks or excessive entry of text. A system according to invention principles addresses these deficiencies and related problems.

SUMMARY OF THE INVENTION

A system provides user prompt menus and candidate user selectable options in a display image on a workstation or system control panel to improve workflow and reduce the number of user interaction steps by predicting a next workflow task. A medical user interface and workflow management system for use in X-ray imaging related procedures includes at least one repository. The at least one repository stores data indicating X-ray imaging related characteristics of a current medical procedure being performed including data identifying a type of procedure, comprising at least one of, (a) a current medical procedure is a cardiac related procedure and (b) a current medical procedure is an Angiography procedure. A workflow processor manages and tracks tasks being performed in a current medical procedure and adaptively selects a next task for performance following completion of a current task by selecting the next task based on the current task and in response to the X-ray imaging related characteristics. A user interface generates data representing at least one display image for presentation to a user. The at least one display image includes image elements associated with the selected next task enabling performance of the selected next task.

DETAILED DESCRIPTION OF THE INVENTION

A medical user interface and workflow management system supports a user in following a workflow task sequence in performing an X-ray imaging related procedure, for example. The system supports a workflow task sequence by prompting a user, via a display image presented on a workstation or system touch panel interface, with a predicted most probable next logical candidate task following completion of a current task. Possible candidate unrelated tasks involving user interaction with the system which does not support a natural task sequence of a specific workflow are suppressed and not made visible to a user in a display image even if the candidate unrelated tasks may be readily accessed. The system advantageously predicts a next workflow task and presents a user with associated information required in performance of the next workflow task and input data entry prompt items supporting user performance of the task and excludes presentation of data concerning non-predicted next tasks. In another embodiment, the system advantageously predicts a plurality of next candidate workflow tasks. In response to user selection of a particular candidate task, the system presents a user with associated information required in performance of the particular next candidate workflow task and input data entry prompt items supporting user performance of the particular next candidate workflow task and excludes presentation of data concerning next tasks other than the particular next candidate workflow task.

A processor as used herein is a device for executing stored machine-readable instructions for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example. A processor may be electrically coupled with any other processor enabling interaction and/or communication there-between. A processor comprising executable instructions may be electrically coupled by being within stored executable instruction enabling interaction and/or communication with executable instructions comprising another processor. A user interface processor or generator is a known element comprising electronic circuitry or software or a combination of both for generating display images or portions thereof. A user interface comprises one or more display images enabling user interaction with a processor or other device.

An executable application comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface 1processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity. An object or data object comprises a grouping of data, executable instructions or a combination of both or an executable procedure.

A workflow processor, as used herein, processes data to determine tasks to add to, or remove from, a task list or modifies tasks incorporated on, or for incorporation on, a task list. A task list is a list of tasks for performance by a worker or device or a combination of both. A workflow processor may or may not employ a workflow engine. A workflow engine, as used herein, is a processor executing in response to predetermined process definitions that implement processes responsive to events and event associated data. The workflow engine implements processes in sequence and/or concurrently, responsive to event associated data to determine tasks for performance by a device and or worker and for updating task lists of a device and a worker to include determined tasks. A process definition is definable by a user and comprises a sequence of process steps including one or more, of start, wait, decision and task allocation steps for performance by a device and or worker, for example. An event is an occurrence affecting operation of a process implemented using a process definition. The workflow engine includes a process definition function that allows users to define a process that is to be followed and includes an Event Monitor, which captures events occurring in a Healthcare Information and Imaging System. A processor in the workflow engine tracks which processes are running, for which patients, and what step needs to be executed next, according to a process definition and includes a procedure for notifying clinicians of a task to be performed, through their worklists (task lists) and a procedure for allocating and assigning tasks to specific users or specific teams.

Figure 1:
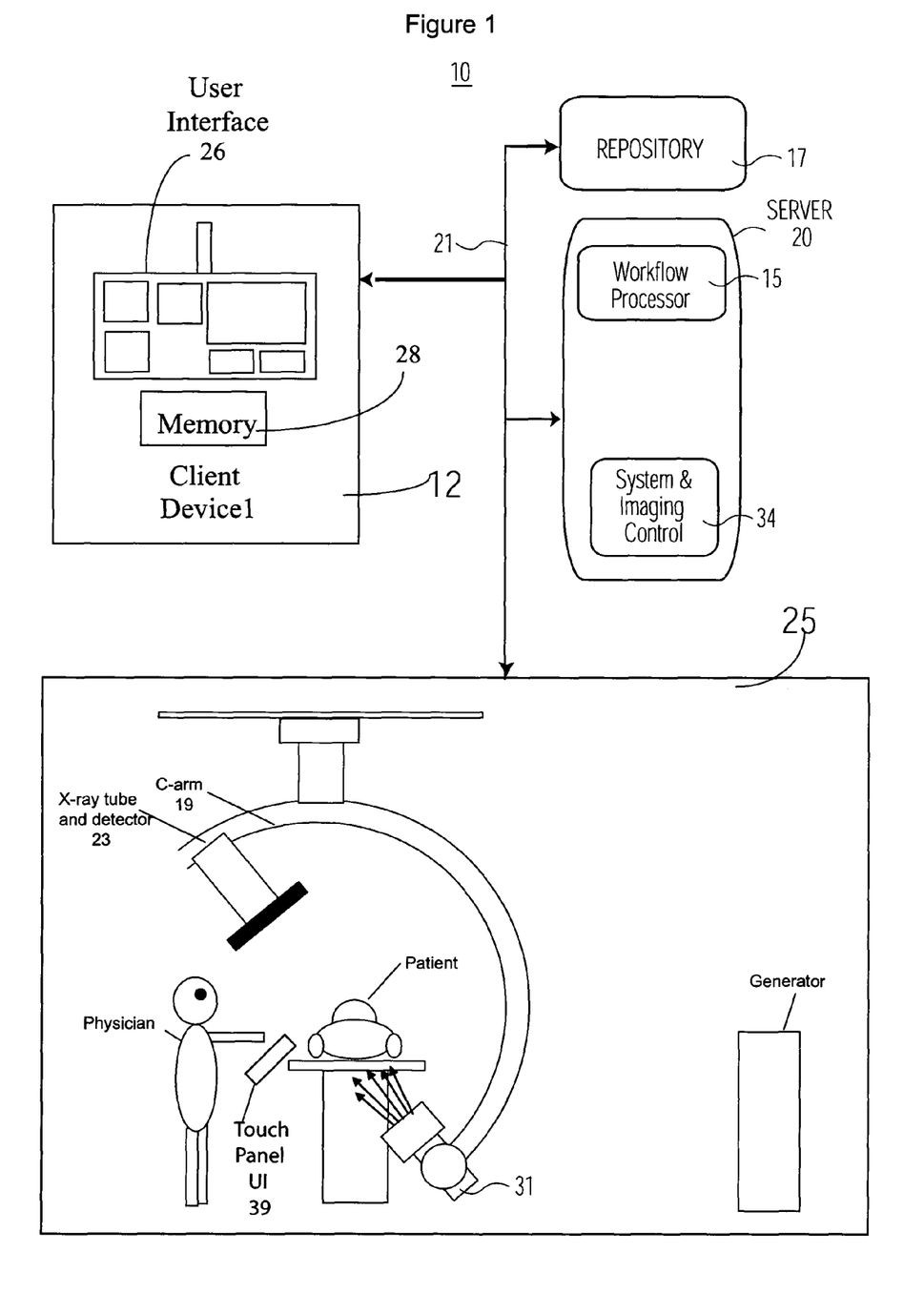
FIG. 1 shows a medical user interface and workflow management system used in a system for performing X-ray imaging related procedures, according to invention principles.

FIG. 1 shows a medical user interface and workflow management system used in system 10 for performing X-ray imaging related procedures. The system is responsive to touch panel system control unit 39 for use in interventional vascular x-ray treatment in cardiac as well as general angiography procedures. System 10 is used in a cardiovascular laboratory or in an interventional angiographic/neurovascular location. System 10 includes one or more processing devices (e.g., workstation or portable device such as notebooks, Personal Digital Assistants, phones) 12 that individually include memory 28 and a user interface 26 supporting image presentation in response to user command entered via touch panel 39 and predetermined user (e.g., physician) specific preferences. System 10 also includes at least one repository 17, X-ray imaging modality system 25 (which in an alternative embodiment may comprise an MR (magnetic resonance), CT scan, or Ultra-sound system, for example) and server 20 intercommunicating via network 21. At least one repository 17 stores data indicating X-ray imaging related characteristics of a current medical procedure being performed and including data identifying a type of procedure. The data identifying a type of procedure comprises data identifying at least one of, (a) a current medical procedure is a cardiac related procedure and (b) a current medical procedure is an Angiography procedure. Further, repository 17 stores medical image studies for multiple patients in DICOM compatible (or other) data format. A medical image study individually includes multiple image series of a patient anatomical portion which in turn individually include multiple images. Server 20 includes workflow processor 15 and system and imaging controller 34.

Workflow processor 15 manages and tracks tasks being performed in a current medical procedure and adaptively selects a next task for performance following completion of a current task by selecting the next task based on the current task and in response to the X-ray imaging related characteristics. User interface 26 generates data representing at least one display image (e.g., a Graphical User Interface (GUI)), for presentation to a user, which may be partitioned into multiple different windows. The at least one display image includes image elements associated with the selected next task enabling performance of the selected next task. System 10 acquires data representing multiple temporally sequential individual images of a patient organ using X-ray imaging modality system 25 for viewing via user interface 26. X-ray modality system 25 comprises C-arm 19 supporting X-ray radiation source 31 and imaging detector device 23 rotating about a patient table. X-ray modality system 25 includes an associated electrical generator for providing electrical power for the X-ray radiation system. Imaging detector 23 detects X-rays provided by source 31 passed through patient anatomy.

In another embodiment, system 10 also comprises integrated systems involving not just X-ray but other imaging modalities, patient monitoring systems and complex procedures involving directing cross-modality and cross-system workflow task sequences that use multiple different imaging modalities and complex procedures. Workflow processor 15 manages and tracks tasks being performed in a current medical procedure using different imaging modalities including, X-ray, MR, CT scan, Ultrasound, PET scan, for example. Such a current medical procedure may comprise a complex procedure in Angiography involving selection and positioning image overlays of prior organ images, stents, catheters and mask images, for example. An X-ray imaging laboratory may comprise integrated patient monitoring, treatment, surgical, imaging and other systems and workflow processor 15 advantageously directs task sequences involving tasks using any or all of these integrated systems.

A cardiac X-ray imaging and treatment laboratory may include a patient monitoring system that supports additional tasks. Workflow processor 15 advantageously directs task sequences involving image or image sequence storage, access, retrieval, update and modification as well as measurement of blood pressure, EKG, pulse rate, blood oxygen saturation, respiratory parameters and other parameters for graphical display, for example. Workflow processor 15 adaptively selects next tasks for performance comprising related tasks that vary in response to, user selection of patient data, documenting medication or patient conditions or stents or other interventional objects to be deployed and in response to performance of other related tasks. Workflow processor 15 automatically adaptively selects a next task for performance based on a type of current task and in response to characteristics related to multiple different imaging modalities, patient monitoring systems and type of medical procedure being performed For instance, X-ray and Ultrasound imaging are often used in conjunction. Ultrasound imaging is used to view an interior vessel surface or determine blood flow and hence its use is selected or ultrasound images are automatically selected by workflow processor 15 for display in conjunction with X-ray procedure related tasks used to determine a next therapeutic task. Workflow processor 15 adaptively directs performance of individual tasks in a sequence comprising an intelligent workflow that advantageously supports the combination of different imaging modality type. Further, workflow processor 15 adaptively selects tasks in an angiography application or a surgical theater, facilitating user navigation through complex procedures involving positioning, image overlays, cross-modality imaging usage and monitored patient parameter driven events, for example. Thereby workflow processor 15 reduces need for cumbersome menu driven lists and task selection.

System 10 in one embodiment comprises a medical user interface and cross-modality workflow management system for use in X-ray imaging and other imaging modality device related procedures. At least one repository 17 stores data indicating imaging modality device related characteristics of a current medical procedure being performed including data identifying a type of procedure as at least one of, a cardiac angiography, general angiography and neuro-vascular angiography procedure and type of imaging modality device being used. Workflow processor 15 adaptively selects a next task for performance in a current medical procedure following completion of a current task by selecting the next task based on the current task and in response to the imaging modality device related characteristics and modality device system configuration data. User interface 26 generates data representing at least one display image for presentation to a user. The at least one display image includes image elements associated with the selected next task enabling performance of the selected next task. In the case of the current medical procedure being an X-ray imaging related procedure workflow processor 15 adaptively selects a next task involving 3D image data processing and adaptively generates data representing at least one display image for presentation to a user, the at least one display image including a window area for display of at least one of, (a) 3D image data and (b) a Digital Subtraction Image. Repository 17 further stores X-ray imaging system configuration data indicating an X-ray imaging system is a bi-plane system and a current imaging system operation mode is a bi-plane mode or a single plane mode.

The at least one display image may comprise an individual image or a sequence of images presenting X-ray, ultrasound, MR or CT scan images of an anatomical feature, for example, or may present medical data or other data as directed by workflow processor 15. Data presented by user interface 26 may include different types of data including data such as measurements associated with a particular image such as a vessel diameter measurement or a value indicating a fall in blood pressure, for example. In response to acquisition of such data, workflow processor 15 automatically prompts a user via the at least one display image, with a correct stent size or prompts the user to initiate a certain medical procedure to address the blood pressure fall. Further, in response to detection of an end of an X-ray imaging acquisition, workflow processor 15 prompt the user via a button in a display image to store associated medical procedure information in an archive such as a PACS (Picture Archiving & Communication System) within repository 17 or alternatively prompts a user to initiate a next X-ray acquisition session.

The activity of adaptively selecting the next task comprises adaptively selecting cross-modality imaging related tasks from a plurality of different tasks associated with different imaging modality devices including at least two of, (a) an MR imaging device, (b) a CT scan imaging device, (c) an ultrasound imaging device, (d) a nuclear PET scanning imaging device and (e) an X-ray imaging device. The activity of adaptively selecting the next task also comprises adaptively selecting a patient monitoring related task associated with the current medical procedure, selecting the patient monitoring related task in response to a value of an acquired patient monitoring parameter and selecting a next task in response to a type of the current medical procedure.

Figure 2:
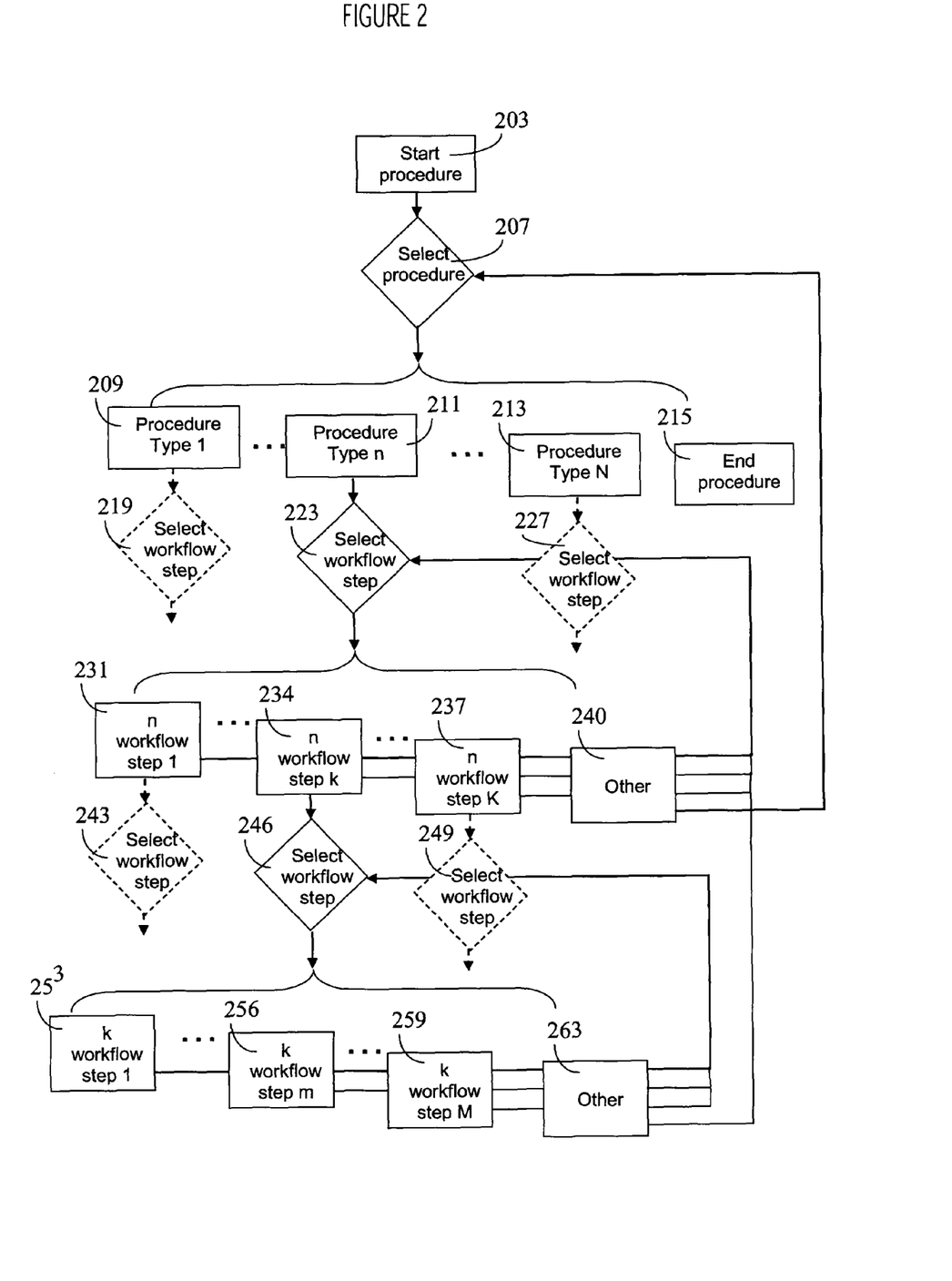
FIG. 2 shows a flowchart of a process for workflow task prediction supporting a workstation image display or control panel image layout, according to invention principles.

FIG. 2 shows a flowchart of a process for workflow task prediction supporting a workstation image display or control panel image layout. The process illustrates three hierarchical levels including a medical procedure level and two workflow levels showing how particular tasks are made available once a medical procedure has been chosen. Alternative embodiments may have only one level, two levels or more than three levels. Following start of a medical procedure in step 203, a user selects a particular procedure 211 (e.g., a cardiac or angiographic procedure) from multiple different procedures in step 207. The multiple different procedures include a first type of procedure 209, an nth type of procedure 211 up to an Nth type of procedure 213, which may include, cardiac angiography, general angiography and neuro-vascular angiography procedures, for example. Repository 17 (FIG. 1) stores data indicating X-ray imaging related characteristics of a current medical procedure being performed. The imaging related characteristics include data identifying the type of procedure. In response to the X-ray imaging related characteristics and selected type of procedure 211, workflow processor 15 adaptively selects next task sequence 223 comprising multiple different tasks 219, 223, 227 for performance. User interface 26 generates data representing at least one display image including image elements associated with selected next task sequence 223 enabling performance of selected next task sequence 223. The image elements include information supporting task performance such as option selection menus, or supporting user data input via a keyboard or mouse, for example, that is presented to a user on a display screen on workstation 12. If a first type of procedure 209 or Nth type of procedure 213 is selected, workflow processor 15 adaptively selects next task sequence 219 or task sequence 227, respectively for performance. Further, in response to user selection of termination of the procedure in step 215 the process of FIG. 2 ends.

Current task sequence 223 in the current medical procedure comprises multiple different tasks 231, 234, 237 and 240. User interface 26 generates data representing at least one display image including image elements associated with individual selected next tasks such as task 234 enabling performance of selected next task 234. The image elements include information supporting task performance as previously described. Following completion of task 240 the process iterates by return to task 223 or procedure selection step 207. Following completion of current task 234 in the current medical procedure, workflow processor 15 adaptively selects next task sequence 246 for performance by selecting next task sequence 246 based on current task 234 and in response to the X-ray imaging related characteristics. User interface 26 generates data representing at least one display image including image elements supporting task performance associated with selected next task sequence 246 enabling performance of selected next task sequence 246. If task sequence 231 or task sequence 237 is selected, workflow processor 15 adaptively selects corresponding next task 243 or task 249, respectively for performance. In response to the X-ray imaging related characteristics and selected next task sequence 246, workflow processor 15 adaptively selects a task sequence comprising multiple different tasks 253, 256, 259 and 263. Following completion of task 263 the process iterates by return to task 246 or task 223 until procedure completion in step 215.

In operation, in response to user selection of particular procedure 211 comprising a cardiac procedure, user interface 26 displays an image excluding image elements related to functions which apply to general angiography procedures (such as buttons to select roadmap, overlay reference and others) and vice versa. During the cardiac procedure 211, after a LV-gram (left ventriculogram) is imaged at the end of a diagnostic phase, workflow processor 15 initiates prompting a user via a displayed image on user interface 26 to select an acquisition program better suited for displaying the coronaries during an interventional phase which may follow the diagnostic phase of the procedure.

User interface 26 also adaptively varies display arrangements of a larger size display image by segmenting it into smaller partitions. If the X-ray system is a bi-plane system (e.g., including two rotatable c-arms), in response to display of the necessary images (fluoroscopy, acquisition, reference images, life-supporting function images), workflow processor 15 automatically initiates display of larger image areas for presentation of medical images and information. If only one plane is used, workflow processor 15 automatically initiates display of smaller image areas for presentation of medical images and information. This is because if both planes are in use, twice the imaging is required (i.e., two fluoroscopy images, two acquisition images, two reference images). In bi-plane operation, if the second plane is moved in, system 10 automatically advantageously prompts a user to select between several candidate display screen arrangements (and similarly when the second plane is moved out again). Further, image elements representing controls for plane 1 or plane 2 or both planes are automatically displayed and made active once plane 1, plane 2 or both planes are moved from parking positions into operating positions (in the vicinity of a patient table).

In operation, in response to user selection of particular procedure 211 (FIG. 2) comprising a neuro-vascular procedure on a bi-plane X-ray imaging system which supports, cardiac angiography, general angiography and neuro-vascular angiography procedures, user interface 26 directed by processor 15, automatically adaptively displays an image reserving display space for three dimensional (3D) application or for display of a DSA (digital subtraction angiography) image on a large area with full pixel resolution. In response to user selection of particular procedure 211 comprising a cardiac procedure on a bi-plane X-ray imaging system, user interface 26 directed by processor 15, automatically adaptively displays one or more images excluding space for 3D image presentation. The one or more images use a larger area presenting fluoroscopic images and present a large image (sequence) with full pixel resolution with which the images were acquired and processed.

Figure 3:
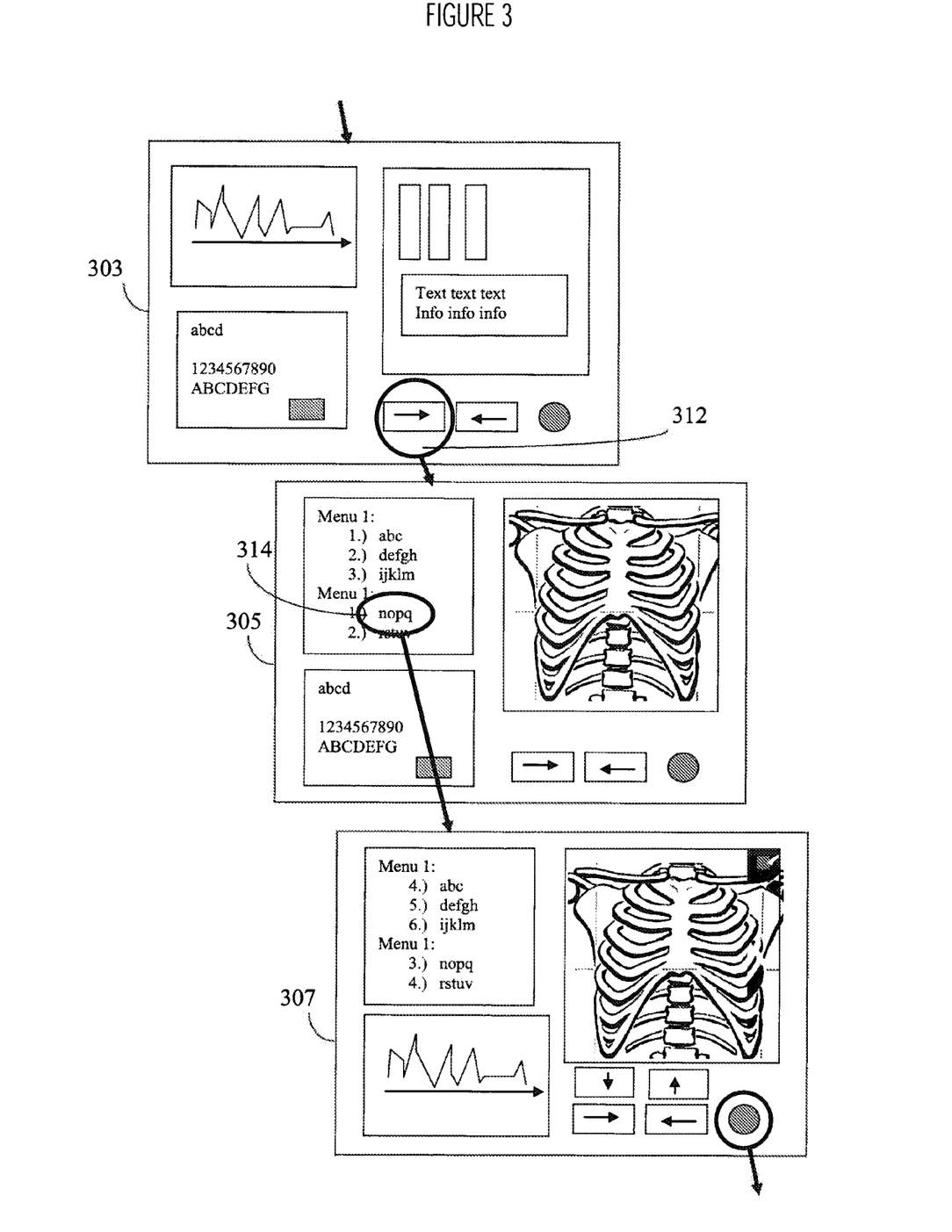
FIG. 3 shows a particular sequence of work steps provided by the medical user interface and workflow management system, according to invention principles.

FIG. 3 shows display images used for performance of a particular sequence of work tasks such as tasks 223, 234 and 246 of FIG. 2 provided by the medical user interface and workflow management system. The display images are presented on user interface 26 (or touch panel 39 in another embodiment). Workflow processor 15 adaptively selects a display image layout and contents presenting candidate next tasks. Workflow processor 15 (FIG. 1) initiates presentation of image display 303 (FIG. 3) on user interface 26 in response to user selection of a task. An image display presented on user interface 26 presents information needed to enable performance of a particular task and excludes information unrelated to the performance of the particular task. The system accommodates input from touch panel 39 as well as a mouse and keyboard. Workflow processor 15 initiates presentation of image display 305 in response to user selection of image element 312 in image display 303. Similarly, workflow processor 15 initiates presentation of image display 307 in response to user selection of image element 314 in image display 305.

Figure 4:
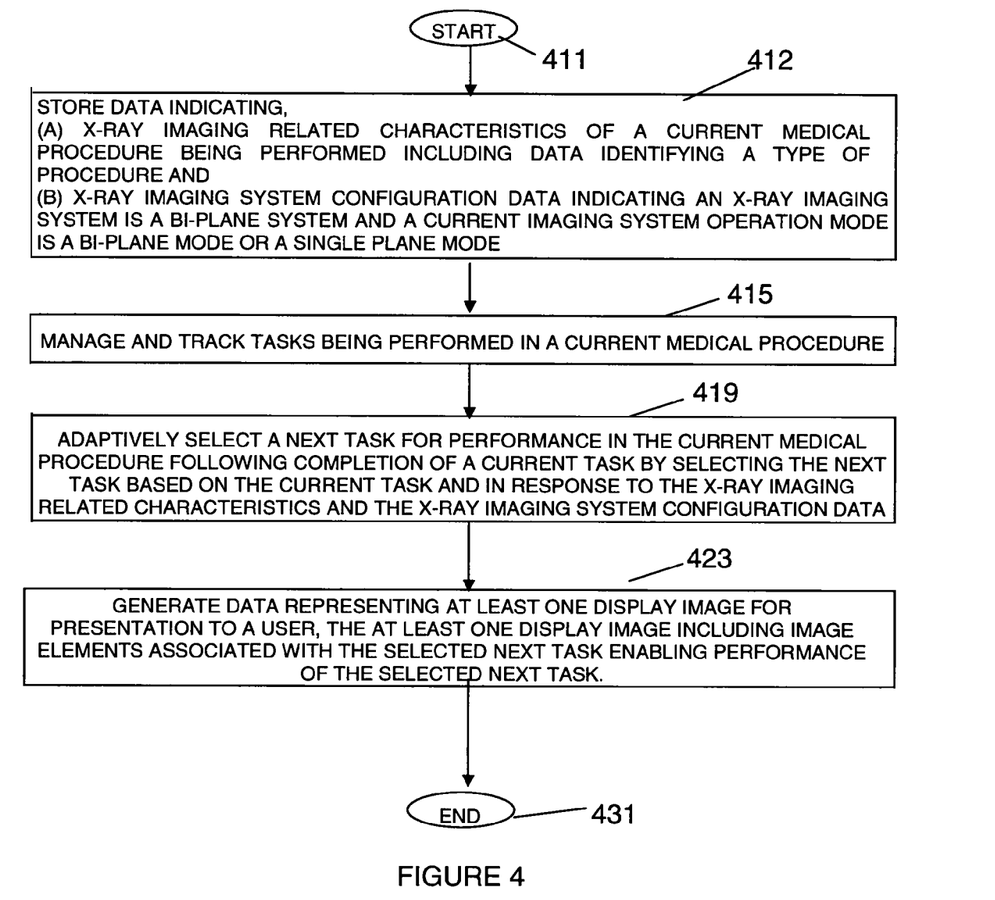
FIG. 4 shows a flowchart of a process used in a medical user interface and workflow management system used in a system for performing X-ray imaging related procedures, according to invention principles.

FIG. 4 shows a flowchart of a process employed by a medical user interface and workflow management system used in a system for performing X-ray imaging related procedures. In step 412, following the start at step 411, system 10 (FIG. 1) stores data indicating, (a) X-ray imaging related characteristics of a current medical procedure being performed including data identifying a type of procedure comprising least one of, a cardiac related, a cardiac angiography, a general angiography and a neuro-vascular angiography procedure and (b) X-ray imaging system configuration data indicating an X-ray imaging system is a bi-plane system and a current imaging system operation mode is a bi-plane mode or a single plane mode. In step 415 workflow processor 15 manages and tracks tasks being performed in a current medical procedure. User interface 26 generates data representing at least one display image including a prompt menu showing user selectable image presentation options adaptively configured for bi-plane operation mode or single plane operation mode. Workflow processor 15 in step 419 adaptively selects a next task (or task sequence) for performance in the current X-ray medical procedure following completion of a current task by selecting the next task based on the current task and in response to the X-ray imaging related characteristics and the X-ray imaging system configuration data. Workflow processor 15 also adaptively selects a next task involving 3D image data processing.

In step 423 user interface 26 generates data representing at least one display image for presentation to a user. The at least one display image includes image elements associated with the selected next task enabling performance of the selected next task. The at least one display image is adaptively configured for presenting, two image windows in response to a bi-plane operation mode or a single image window in response to a single plane operation mode and is adaptively configured for presenting image elements enabling bi-plane imaging controls, in response to detection both C-arms of an X-ray imaging system are in operational position or in response to a bi-plane operation mode. A display image also includes a window area for display of at least one of, (a) 3D image data and (b) a Digital Subtraction Image. The display image also includes a prompt menu showing user selectable image presentation options adaptively configured for bi-plane operation mode or single plane operation mode. The process of FIG. 4 terminates at step 431.

In response to the X-ray imaging related characteristics indicating the current medical procedure is a cardiac related procedure, workflow processor 15 adaptively selects a next task for performance excluding tasks relating to general Angiography and user interface 26 generates data representing a display image excluding image elements associated with general Angiography. Similarly, in response to the X-ray imaging related characteristics indicating the current medical procedure is a diagnostic cardiac related procedure, workflow processor 15 adaptively selects a next task for performance comprising initiating imaging examination of coronary arteries and user interface 26 generates data representing a display image presenting acquired image data of coronary arteries.

The systems and processes of FIGS. 1-4 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system is advantageously used for post-processing and diagnostic analysis of medical images or reporting systems for online documentation of an interventional medical procedure (wire in, stent of a given type and size deployed, medication given, blood pressure recorded, etc.). The processes and applications may, in alternative embodiments, be located on one or more (e.g., distributed) processing devices accessing a network linking the elements of FIG. 1. Further, any of the functions and steps provided in FIGS. 1-4 may be implemented in hardware, software or a combination of both and may reside on one or more processing devices located at any location of a network linking the elements of FIG. 1 or another linked network, including the Internet.

What is claimed is:

1. A medical user interface and workflow management system for use in X-ray imaging and other imaging modality related procedures, comprising:
    at least one repository configured to store data indicating X-ray imaging related characteristics of a current medical procedure being performed including data identifying a type of procedure, comprising at least one of, (a) a current medical procedure is a cardiac related procedure and (b) a current medical procedure is an Angiography procedure; and
    at least one processing device including,
        a workflow processor configured to manage imaging device operation workflows comprising sequences of tasks and tracking progress of tasks being performed in a current medical procedure task sequence by tracking running processes, steps to be executed next by a worker or device and completion of tasks and for updating task lists and using the stored data in adaptively selecting a next task of a plurality of tasks of said current medical procedure for performance following completion of a current task by selecting a first task as said next task based on said current task if said current medical procedure being performed is a cardiac related procedure and by selecting a different second task as said next task if said current medical procedure being performed is an Angiography procedure and
        a user interface configured to generate data representing at least one display image for presentation to a user, said at least one display image identifying the selected next task and including image elements associated with the selected next task enabling performance of the selected next task.

2. A system according to claim 1, wherein
said at least one repository stores X-ray imaging system configuration data indicating said X-ray imaging system is a bi-plane system and
said workflow processor adaptively selects said next task based on said current task and in response to said X-ray imaging related characteristics and said configuration data.

3. A system according to claim 1, wherein
in response to said X-ray imaging related characteristics indicating said current medical procedure is a cardiac related procedure, said workflow processor adaptively selects a next task for performance excluding tasks relating to general Angiography and
said user interface generates data representing a display image excluding image elements associated with general Angiography.

4. A system according to claim 1, wherein
in response to said X-ray imaging related characteristics indicating said current medical procedure is a diagnostic cardiac related procedure, said workflow processor adaptively selects a next task for performance comprising initiating imaging examination of coronary arteries and
said user interface generates data representing a display image presenting acquired image data of coronary arteries.

5. A system according to claim 1, wherein
said at least one repository stores X-ray imaging system configuration data indicating said X-ray imaging system is a bi-plane system and a current imaging system operation mode is a bi-plane mode or a single plane mode and
said user interface generates data representing at least one display image adaptively configured for presenting, two image windows in response to a bi-plane operation mode or a single image window in response to a single plane operation mode.

6. A system according to claim 5, wherein
said user interface generates data representing at least one display image adaptively configured for presenting image elements enabling bi-plane imaging controls, in response to a bi-plane operation mode.

7. A system according to claim 5, wherein
said user interface generates data representing at least one display image adaptively configured for presenting image elements enabling bi-plane imaging controls, in response to detection both C-arms of an X-ray imaging system are in operational position.

8. A system according to claim 1, wherein
said at least one repository stores X-ray imaging system configuration data indicating said X-ray imaging system is a bi-plane system and a current imaging system operation mode is a bi-plane mode or a single plane mode and
said user interface generates data representing at least one display image including a prompt menu showing user selectable image presentation options adaptively configured for bi-plane operation mode or single plane operation mode.

9. A system according to claim 1, wherein
said X-ray imaging related characteristics of a current medical procedure being performed include data identifying a type of procedure, comprising a current medical procedure is a neuro-vascular Angiography procedure, said workflow processor adaptively selects a next task involving 3D image data processing and
said user interface adaptively generates data representing at least one display image for presentation to a user, said at least one display image including a window area for display of at least one of, (a) 3D image data and (b) a Digital Subtraction Image.

10. A method employed by a medical user interface and workflow management system for use in X-ray imaging and other imaging modality related procedures, the method comprising the activities of,
employing at least one computer for:
storing data in at least one repository indicating,
(a) X-ray imaging related characteristics of a current medical procedure being performed including data identifying a type of procedure and
(b) X-ray imaging system configuration data indicating an X-ray imaging system is a bi-plane system and a current imaging system operation mode is a bi-plane mode or a single plane mode;
managing imaging device operation workflows comprising sequences of tasks;
tracking progress of tasks being performed in a current medical procedure task sequence of a workflow by tracking running processes, steps to be executed next by a worker or device and completion of tasks;
using the stored data in adaptively selecting a next task of a plurality of tasks of said current medical procedure for performance in the current medical procedure following completion of a current task by selecting a first task as said next task based on said current task if said current medical procedure being performed is a cardiac related procedure and by selecting a different second task as said next task if said current medical procedure being performed is an Angiography procedure; and
generating data representing at least one display image for presentation to a user, said at least one display image identifying the selected next task and including image elements associated with the selected next task enabling performance of the selected next task.

11. A method according to claim 10, wherein
said X-ray imaging related characteristics of said current medical procedure indicate at least one of, (a) a current medical procedure is a cardiac related procedure and (b) a current medical procedure is an Angiography procedure.

12. A method according to claim 10, including the activity of
generating data representing at least one display image adaptively configured for presenting, two image windows in response to a bi-plane operation mode or a single image window in response to a single plane operation mode, based on said X-ray imaging system configuration data.

13. A method according to claim 12, including the activity of generating data representing at least one display image adaptively configured for presenting image elements enabling bi-plane imaging controls, in response to a bi-plane operation mode.

14. A method according to claim 10, including the activity of
generating data representing at least one display image adaptively configured for presenting image elements enabling bi-plane imaging controls, in response to detection both C-arms of an X-ray imaging system are in operational position.

15. A method according to claim 10, wherein
said X-ray imaging related characteristics of a current medical procedure being performed include data identifying a type of procedure, comprising a current medical procedure is a neuro-vascular Angiography procedure, including the activities of
adaptively selecting a next task involving 3D image data processing and
adaptively generating data representing at least one display image for presentation to a user, said at least one display image including a window area for display of at least one of, (a) 3D image data and (b) a Digital Subtraction Image.

16. A method employed by a medical user interface and cross-modality workflow management system for use in X-ray imaging and other imaging modality device related procedures, the method comprising the activities of
employing at least one computer for:
storing data in at least one repository indicating imaging modality device related characteristics of a current medical procedure being performed including data identifying a type of procedure as at least one of, a cardiac angiography, general angiography and neuro-vascular angiography procedure and type of imaging modality device being used;
tracking progress of tasks being performed in a current medical procedure task sequence of an imaging device operation workflow by tracking running processes, steps to be executed next by a worker or device and completion of tasks and for updating task lists;
using the stored data in adaptively selecting a next task of a plurality of tasks of a current medical procedure for performance in said current medical procedure following completion of a current task by selecting a first task as said next task based on said current task if said current medical procedure being performed is a cardiac related procedure and by selecting a different second task as said next task if said current medical procedure being performed is an Angiography procedure and in response to said imaging modality device related characteristics and modality device system configuration data; and
generating data representing at least one display image for presentation to a user, said at least one display image identifying the selected next task and including image elements associated with the selected next task enabling performance of the selected next task.

17. A method according to claim 16, wherein
said current medical procedure is an X-ray imaging related procedure and including the activities of
adaptively selecting a next task involving 3D image data processing and
adaptively generating data representing at least one display image for presentation to a user, said at least one display image including a window area for display of at least one of, (a) 3D image data and (b) a Digital Subtraction Image.

18. A method according to claim 16, wherein
said current medical procedure is an X-ray imaging related procedure and including the activity of
storing X-ray imaging system configuration data indicating an X-ray imaging system is a bi-plane system and a current imaging system operation mode is a bi-plane mode or a single plane mode.

19. A method according to claim 16, wherein
said activity of adaptively selecting said next task comprises adaptively selecting cross-modality imaging related tasks from a plurality of different tasks associated with different imaging modality devices including at least two of, (a) an MR imaging device, (b) a CT scan imaging device, (c) an ultrasound imaging device, (d) a nuclear PET scanning imaging device and (e) an X-ray imaging device.

20. A method according to claim 19, wherein
said activity of adaptively selecting said next task comprises adaptively selecting a patient monitoring related task associated with said current medical procedure.

21. A method according to claim 19, wherein
said activity of adaptively selecting said next task comprises adaptively selecting said patient monitoring related task in response to a value of an acquired patient monitoring parameter.

22. A method according to claim 19, wherein
said activity of adaptively selecting said next task comprises adaptively selecting a next task in response to a type of said current medical procedure.

23. A method according to claim 16, including the activity of
prompting a user via a displayed image to select an image acquisition program better suited for an identified clinical application.

\* \* \* \* \*